(12) United States Patent
Borch et al.

(10) Patent No.: US 7,465,570 B2
(45) Date of Patent: Dec. 16, 2008

(54) VARIANT LIPOLYTIC ENZYMES

(75) Inventors: Kim Borch, Birkerod (DK); Luise Erlandsen, Copenhagen V (DK); Jesper Vind, Vaerlose (DK); Allan Svendsen, Horsholm (DK); Christel Thea Jorgensen, Kgs Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 153 days.

(21) Appl. No.: 10/556,511

(22) PCT Filed: Apr. 29, 2004

(86) PCT No.: PCT/DK2004/000292

§ 371 (c)(1),
(2), (4) Date: Nov. 9, 2005

(87) PCT Pub. No.: WO2004/099400

PCT Pub. Date: Nov. 18, 2004

(65) Prior Publication Data

US 2006/0228446 A1    Oct. 12, 2006

Related U.S. Application Data

(60) Provisional application No. 60/479,647, filed on Jun. 3, 1920, provisional application No. 60/474,881, filed on May 30, 2003, provisional application No. 60/469,228, filed on May 9, 2003.

(30) Foreign Application Priority Data

May 9, 2003   (DK) .............................. 2003 00709
May 30, 2003  (DK) .............................. 2003 00811

(51) Int. Cl.
*C12N 9/16*   (2006.01)
*A21D 8/02*   (2006.01)

(52) U.S. Cl. ........................................ 435/196; 426/20
(58) Field of Classification Search ................ 435/198, 435/196

See application file for complete search history.

(56) References Cited

FOREIGN PATENT DOCUMENTS

| EP | 0 869 167 | 10/1998 |
|---|---|---|
| WO | WO 98/26057 | 6/1998 |
| WO | WO 00/32758 | 6/2000 |
| WO | WO 01/83770 | 11/2001 |
| WO | WO 02/00852 | 1/2002 |
| WO | WO 02/055679 | 7/2002 |

*Primary Examiner*—Tekchand Saidha
(74) *Attorney, Agent, or Firm*—Kristin J. McNamara

(57) ABSTRACT

The inventors have developed improved polypeptides by substituting or deleting specified amino acids in fungal lipolytic enzymes. More particularly, the polypeptides result in a reduction of dough stickiness when they are added to a dough. The polypeptides may particularly have activity on polar lipids.

15 Claims, 3 Drawing Sheets

Figure 1.

Alignment of fungal lipolytic enzyme sequences

```
                   1                                                    50
SEQ ID NO:  1   ........AV  GVTTTDFSNF  KFYIQHGAAA  .......YC.  .NSEAAAGSK    33
SEQ ID NO:  2   ..........  EVSQDLFNQF  NLFAQYSAAA  .......YCG  KNNDAPAGTN    33
SEQ ID NO:  3   SSSSTQDYRI  ASEAEIKAHT  FYTALSANA.  .......YCR  TVIPG.....
SEQ ID NO:  4   .SSSTQDYRI  ASEAEIKAHT  FYTALSANA.  .......YCR  TVIPG.....
SEQ ID NO:  5   ..SIDGGIRA  ATSQEINELT  YYTTLSANS.  .......YCR  TVIPG.....
SEQ ID NO:  6   .SASDGGKVV  AATTAQIQEF  TKYAGIAATA  .......YCR  SVVPG.....
SEQ ID NO:  7   ....TAGHAL  AASTQ.GISE  DLYSRL.VEM  ATISQAAYAD  LCNIPST...
SEQ ID NO:  8   ....TAGHAL  AASTQ.GISE  DLYSRL.VEM  ATISQAAYAD  LCNIPST...
SEQ ID NO:  9   ........AV  TVTTQDLSNF  RFYLQHADAA  .......YC.  .NFNTAVGKP
SEQ ID NO: 10   ..........  DIPTTQLEDF  KFWVQYAAAT  .......YCP  NNYVAKDGEK
SEQ ID NO: 11   ..........  DVSTSELDQF  EFWVQYAAAS  .......YYE  ADYTAQVGDK
SEQ ID NO: 12   ..........  SVSTSTLDEL  QLFAQWSAAA  .......YCS  NNID.SKDSN
SEQ ID NO: 13   ..........  SVSTSTLDEL  QLFSQWSAAA  .......YCS  NNID.SDDSN
SEQ ID NO: 14   ..........  DVSSSLLNNL  DLFAQYSAAA  .......YCD  ENLN.STGTK
SEQ ID NO: 15   ..........  EVSQDLFNQF  NLFAQYSAAA  .......YCG  KNNDAPAGTN    33

51                                                  100
SEQ ID NO:  1   ITCSNNGCPT  VQGNGATIVT  SF..VGSKTG  IGGYVATDSA  RKEIVVSFRG    81
SEQ ID NO:  2   ITCTGNACPE  VEKADATFLY  SFE.DSGVGD  VTGFLALDNT  NKLIVLSFRG    82
SEQ ID NO:  3   GRWSCPHCGV  AS..NLQITK  TFST..LITD  TNVLVAVGEK  EKTIYVVFRG
SEQ ID NO:  4   GQWSCPHCDV  AP..NLNITK  TFTT..LITD  TNVLVAVGEN  EKTIYVVFRG
SEQ ID NO:  5   ATWDCIHCDA  TE..DLKIIK  TWST..LIYD  TNAMVARGDS  EKTIYIVFRG
SEQ ID NO:  6   NKWDCVQCQK  WVP.DGKIIT  TFTS..LLSD  TNGYVLRSDK  QKTIYLVFRG
SEQ ID NO:  7   ..........  ......IIK   GEKIYNSQTD  INGWILRDDS  SKEIITVFRG
SEQ ID NO:  8   ..........  ......IIK   GEKIYNSQTD  INGWILRDDS  SKEIITVFRG
SEQ ID NO:  9   VHCSAGNCPD  IEKDAAIVVG  SV..VGTKTG  IGAYVATDNA  RKEIVVSVRG
SEQ ID NO: 10   LNCSVGNCPD  VEAAGSTVKL  SFS.DDTITD  TAGFVAVDNT  NKAIVVAFRG
SEQ ID NO: 11   LSCSKGNCPE  VEATGATVSY  DFS.DSTITD  TAGYIAVDHT  NSAVVLAFRG
SEQ ID NO: 12   LTCTANACPS  VEEASTTMLL  EFDLTNDFGG  TAGFLAADNT  NKRLVVAFRG
SEQ ID NO: 13   VTCTADACPS  VEEASTKMLL  EFDLTNNFGG  TAGFLAADNT  NKRLVVAFRG
SEQ ID NO: 14   LTCSVGNCPL  VEAASTQSLD  EFNESSSYGN  PAGYLAADET  NKLLVLSFRG
SEQ ID NO: 15   ITCTGNACPE  VEKADATFLY  SFE.DSGVGD  VTGFLALDNT  NKLIVLSFRG    82

101                                                 150
SEQ ID NO:  1   SINIRNWLTN  LDFG.QEDCS  L..VSGCGVH  SGFQRAWNEI  SSQATAAVAS   128
SEQ ID NO:  2   SRSIENWIAN  LNFWLKKIND  I..CSGCRGH  DGFTSSWRSV  ADTLRQKVED   130
SEQ ID NO:  3   TSSIRNAIAD  IVFVPVNYPP  V...NGAKVH  KGFLDSYNEV  QDKLVAEVKA
SEQ ID NO:  4   TSSIRNAIAD  IVFVPVNYPP  V...NGAKVH  KGFLDSYNEV  QDKLVAEVKA
SEQ ID NO:  5   SSSIRNWIAD  LTFVPVSYPP  V...SGTKVH  KGFLDSYGEV  QNELVATVLD
SEQ ID NO:  6   TNSFRSAITD  IVFNFSDYKP  V...KGAKVH  AGFLSSYEQV  VNDYFPVVQE
SEQ ID NO:  7   TGSDTNLQLD  TNYTLTPFDT  LPQCNGCEVH  GGYYIGWVSV  QDQVESLVKQ
SEQ ID NO:  8   TGSDTNLQLD  TNYTLTPFDT  LPQCNSCEVH  GGYYIGWISV  QDQVESLVQQ
SEQ ID NO:  9   SINVRNWITN  FNFG.QKTCD  L..VAGCGVH  TGFLDAWEEV  AANVKAAVSA
SEQ ID NO: 10   SYSIRNWVTD  ATFP.QTDPG  L..CDGCKAE  LGFWTAWKVV  RDRIIKTLDE
SEQ ID NO: 11   SYSVRNWVAD  ATFV.HTNPG  L..CDGCLAE  LGFWSSWKLV  RDDIIKELKE
SEQ ID NO: 12   SSTIENWIAN  LDFILEDNDD  L..CTGCKVH  TGFWKAWESA  ADELTSKIKS
SEQ ID NO: 13   SSTIKNWIAD  LDFILQDNDD  L..CTGCKVH  TGFWKAWEAA  ADNLTSKIKS
SEQ ID NO: 14   SADLANWVAN  LNFGLEDASD  L..CSGCEVH  SGFWKAWSEI  ADTITSKVES
SEQ ID NO: 15   SRSIENWIGN  LNFDLKEIND  I..CSGCRGH  DGFTSSWRSV  ADTLRQKVED   130
```

Fig. 1 cont.

```
              151                                                        200
SEQ ID NO: 1  ARKANPSFNV ISTGHSLGGA VAVLAAANLR VGGT.....P VDIYTYGSPR     173
SEQ ID NO: 2  AVREHPDYRV VFTGHSLGGA LATVAGADLR GNGY.....D IDVFSYGAPR     175
SEQ ID NO: 3  QLDRHPGYKI VVTGHSLGGA TAVLSALDLY HHGHA....N IEIYTQGQPR
SEQ ID NO: 4  QLDRHPGYKI VVTGHSLGGA TAVLSALDLY HHGHD....N IEIYTQGQPR
SEQ ID NO: 5  QFKQYPSYKV AVTGHSLGGA TALLCALDLY QREEGLSSSN LFLYTQGQPR
SEQ ID NO: 6  QLTAHPTYKV IVTGHSLGGA QALLAGMDLY QREPRLSPKN LSIFTVGGPR
SEQ ID NO: 7  QVSQYPDYAL TVTGHSLGAS LAALTAAQL. SATYD....N IRLYTFGEPR
SEQ ID NO: 8  QVSQFPDYAL TVTGHSLGAS LAALTAAQL. SATYD....N IRLYTFGEPR
SEQ ID NO: 9  AKTANPTFKF VVTGHSLGGA VATIAAAYLR KDGF.....P FDLYTYGSPR
SEQ ID NO: 10 LKPEHSDYKI VVVGHSLGAA IASLAAADLR TKNY.....D AILYAYAAPR
SEQ ID NO: 11 VVAQNPNYEL VVVGHSLGAA VATLAATDLR GKGYP....S AKLYAYASPR
SEQ ID NO: 12 AMSTYSGYTL YFTGHSLGGA LATLGATVLR NDGY.....S VELYTYGCPR
SEQ ID NO: 13 AMSTYSGYTL YFTGHSLGGA LATLGATVLR NDGY.....S VELYTYGCPR
SEQ ID NO: 14 ALSDHSDYSL VLTGHSYGAA LAALAATALR NSGH.....S VELYNYGQPR
SEQ ID NO: 15 AVREHPDYRV VFTGHSLGGA LATVAGADLR GNGY.....D IDVFSYGAPR     175

201                                                        250
SEQ ID NO: 1  VGNAQLSAFV SNQ....... AGGEYRVTHA DDPVPRLPPL IFGYRHTTPE     216
SEQ ID NO: 2  VGNRAFAEFL TVQ......T GGTLYRITHT NDIVPRLPPR EFGYSHSSPE     219
SEQ ID NO: 3  IGTPAFANYV IGT....... KIPYQRLVHE RDIVPHLPPG AFGFLHAGEE
SEQ ID NO: 4  IGTPEFANYV IGT....... KIPYQRLVNE RDIVPHLPPG AFGFLHAGEE
SEQ ID NO: 5  VGDPAFANYV VST....... GIPYRRTVNE RDIVPHLPPA AFGFLHAGEE
SEQ ID NO: 6  VGNPTFAYYV EST....... GIPFQRTVHK RDIVPHVPPQ SFGFLHPGVE
SEQ ID NO: 7  SGNQAFASYM NDAFQASSPD TTQYFRVTHA NDGIPNLPPV EQGYAHGGVE
SEQ ID NO: 8  S.NQAFASYM NDAFQASSPD TTQYFRVTHA NDGIPNLPPA DEGYAHGVVE
SEQ ID NO: 9  VGNDFFANFV TQQ....... TGAEYRVTHG DDPVPRLPPI VFGYRHTSPE
SEQ ID NO: 10 VANKPLAEFI TNQ....... .GNNYRFTHN DDPVPKLPLL TMGYVHISPE
SEQ ID NO: 11 VGNAALAKYI TAQ....... .GNNFRFTHT NDPVPKLPLL SMGYVHVSPE
SEQ ID NO: 12 IGNYALAEHI TSQ......G SGANFRVTHL NDIVPRVPPM DFGFSQPSPE
SEQ ID NO: 13 VGNYALAEHI TSQ......G SGANFPVTHL NDIVPRVPPM DFGFSQPSPE
SEQ ID NO: 14 LGNEALATYI TDQ......N KGGNYRVTHT NDIVPKLPPT LLGYHHFSPE
SEQ ID NO: 15 VGNRAFAEFL TVQ......T GGTLYRITHT NDIVPRLPPR EFGYSHSSPE     219

251                                                        300
SEQ ID NO: 1  FWLSGGGGDK VDYTISDVKV CEGAANLG.C NGGTLGL... DIAAHLHYF.    261
SEQ ID NO: 2  YWIKS..GTL VPVTRNDIVK IEGIDATG.G NNQPNIP... DIPAHLWYF.    262
SEQ ID NO: 3  FWIMK..... .....DSSLRV CPNGIETDNC SNSIVPFT.. SVIDHLSYLD
SEQ ID NO: 4  FWIMK..... .....DSSLRV CPNGIETDNC SNSIVPFT.. SVIDHLSYLD
SEQ ID NO: 5  YWITD..... ..NSPETVQV CTSDLETSDC SNSIVPFT.. SVLDHLSYFG
SEQ ID NO: 6  SWIKS..... ...GTSNVQI CTSEIETKDC SNSIVPFT.. SILDHLSYFD
SEQ ID NO: 7  YWSV....DP YSAQNTFVCT GDEVQCCE.A QGGQGVN... ..NAHTTYF.
SEQ ID NO: 8  YWSV....DP YSAQNTFVCT GDEVQCCE.A QGGQGVN... ..NAHTTYF.
SEQ ID NO: 9  YWLNG.GPLD KDYTVTEIKV CEGIANVM.C NGGTIGL... DILAHITYF.
SEQ ID NO: 10 YYITA..PDN TTVTDNQVTV LDGYVNFK.G NTGTSGGLPD LLAFHSHVWY
SEQ ID NO: 11 YWITS..PNN ATVSTSDIKV IDGDVSFD.G NTGTGLPLLT DFEAHIWYF.
SEQ ID NO: 12 YWITS..GNG ASVTASDIEV IEGINSTA.G NAGEATV... SVLAHLWYF.
SEQ ID NO: 13 YWITS..GTG ASVTASDIEL IEGINSTA.G NAGEATV... DVLAHLWYF.
SEQ ID NO: 14 YYISS..ADE ATVTTDVTE VTGIDATG.G NDGTDGT... SIDAHRWYF.
SEQ ID NO: 15 YWIKS..GTL VPVTRNDIVK IEGIDATG.G NNQPNIP... DIPAHLWYF.    262
```

Fig. 1 cont.

```
                   301                                             350
SEQ ID NO: 1    QATDA.CNAG GFS.......  .......... .........  ........   286
SEQ ID NO: 2    QATDA.CNAG GFS.......  .......... .........  ........   269
SEQ ID NO: 3    MNTGL.CL..  .......... .......... .........  ........
SEQ ID NO: 4    MNTGL.CL..  .......... .......... .........  ........
SEQ ID NO: 5    INTGL.CT..  .......... .......... .........  ........
SEQ ID NO: 6    INEGS.CL..  .......... .......... .........  ........
SEQ ID NO: 7    GMTSGACTW.  .......... .......... .........  ........
SEQ ID NO: 8    GMTSGHCTW
SEQ ID NO: 9    QSMAT.CAPI AIPWKR....  .......... .........  ........
SEQ ID NO: 10   FIHADACKGP GLPLR.....  .......... .........  ........
SEQ ID NO: 11   VQVDAGKGPG LPFKR.....  .......... .........  ........
SEQ ID NO: 12   FAISE.CLL.  .......... .......... .........  ........
SEQ ID NO: 13   FAISE.CLL.  .......... .......... .........  ........
SEQ ID NO: 14   IYISE.CS..  .......... .......... .........  ........
SEQ ID NO: 15   GLIGT.CL..  .......... .......... .........  ........   269
```

SEQUENCE LISTING

<160> NUMBER OF SEQ ID NOS: 15

<210> SEQ ID NO 1
<211> LENGTH: 286
<212> TYPE: PRT
<213> ORGANISM: Fusarium oxysporum

<400> SEQUENCE: 1

Ala Val Gly Val Thr Thr Thr Asp Phe Ser Asn Phe Lys Phe Tyr Ile
1               5                   10                  15

Gln His Gly Ala Ala Ala Tyr Cys Asn Ser Glu Ala Ala Gly Ser
            20                  25                  30

Lys Ile Thr Cys Ser Asn Asn Gly Cys Pro Thr Val Gln Gly Asn Gly
                35                  40                  45

Ala Thr Ile Val Thr Ser Phe Val Gly Ser Lys Thr Gly Ile Gly Gly
        50                  55                  60

Tyr Val Ala Thr Asp Ser Ala Arg Lys Glu Ile Val Val Ser Phe Arg
65                  70                  75                  80

Gly Ser Ile Asn Ile Arg Asn Trp Leu Thr Asn Leu Asp Phe Gly Gln
                85                  90                  95

Glu Asp Cys Ser Leu Val Ser Gly Cys Gly Val His Ser Gly Phe Gln
            100                 105                 110

Arg Ala Trp Asn Glu Ile Ser Ser Gln Ala Thr Ala Ala Val Ala Ser
        115                 120                 125

Ala Arg Lys Ala Asn Pro Ser Phe Asn Val Ile Ser Thr Gly His Ser
130                 135                 140

Leu Gly Gly Ala Val Ala Val Leu Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Pro Leu Ile Phe
        195                 200                 205

Gly Tyr Arg His Thr Thr Pro Glu Phe Trp Leu Ser Gly Gly Gly Gly
    210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

```
His Leu His Tyr Phe Gln Ala Thr Asp Ala Cys Asn Ala Gly Gly Phe
            260                 265                 270

Ser Trp Arg Arg Tyr Arg Ser Ala Glu Ser Val Asp Lys Arg
        275                 280                 285

<210> SEQ ID NO 2
<211> LENGTH: 274
<212> TYPE: PRT
<213> ORGANISM: Artificial
<220> FEATURE:
<223> OTHER INFORMATION: Variant disclosed in WO 0032758

<400> SEQUENCE: 2

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Ala Asn Leu Asn Phe Trp
                85                  90                  95

Leu Lys Lys Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gln Ala Thr Asp Ala Cys Asn Ala Gly Gly
            260                 265                 270

Phe Ser

<210> SEQ ID NO 3
<211> LENGTH: 265
<212> TYPE: PRT
<213> ORGANISM: Absidia reflexa

<400> SEQUENCE: 3

Ser Ser Ser Ser Thr Gln Asp Tyr Arg Ile Ala Ser Glu Ala Glu Ile
```

```
1               5                  10                 15
Lys Ala His Thr Phe Tyr Thr Ala Leu Ser Ala Asn Ala Tyr Cys Arg
                20                 25                 30

Thr Val Ile Pro Gly Gly Arg Trp Ser Cys Pro His Cys Gly Val Ala
                35                 40                 45

Ser Asn Leu Gln Ile Thr Lys Thr Phe Ser Thr Leu Ile Thr Asp Thr
    50                 55                 60

Asn Val Leu Val Ala Val Gly Glu Lys Glu Lys Thr Ile Tyr Val Val
65                 70                 75                 80

Phe Arg Gly Thr Ser Ser Ile Arg Asn Ala Ile Ala Asp Ile Val Phe
                85                 90                 95

Val Pro Val Asn Tyr Pro Pro Val Asn Gly Ala Lys Val His Lys Gly
                100                105                110

Phe Leu Asp Ser Tyr Asn Glu Val Gln Asp Lys Leu Val Ala Glu Val
                115                120                125

Lys Ala Gln Leu Asp Arg His Pro Gly Tyr Lys Ile Val Val Thr Gly
                130                135                140

His Ser Leu Gly Gly Ala Thr Ala Val Leu Ser Ala Leu Asp Leu Tyr
145                150                155                160

His His Gly His Ala Asn Ile Glu Ile Tyr Thr Gln Gly Gln Pro Arg
                165                170                175

Ile Gly Thr Pro Ala Phe Ala Asn Tyr Val Ile Gly Thr Lys Ile Pro
                180                185                190

Tyr Gln Arg Leu Val His Glu Arg Asp Ile Val Pro His Leu Pro Pro
                195                200                205

Gly Ala Phe Gly Phe Leu His Ala Gly Glu Glu Phe Trp Ile Met Lys
                210                215                220

Asp Ser Ser Leu Arg Val Cys Pro Asn Gly Ile Glu Thr Asp Asn Cys
225                230                235                240

Ser Asn Ser Ile Val Pro Phe Thr Ser Val Ile Asp His Leu Ser Tyr
                245                250                255

Leu Asp Met Asn Thr Gly Leu Cys Leu
                260                265

<210> SEQ ID NO 4
<211> LENGTH: 264
<212> TYPE: PRT
<213> ORGANISM: Absidia corymbifera

<400> SEQUENCE: 4

Ser Ser Ser Thr Gln Asp Tyr Arg Ile Ala Ser Glu Ala Glu Ile Lys
1               5                  10                 15

Ala His Thr Phe Tyr Thr Ala Leu Ser Ala Asn Ala Tyr Cys Arg Thr
                20                 25                 30

Val Ile Pro Gly Gly Gln Trp Ser Cys Pro His Cys Asp Val Ala Pro
                35                 40                 45

Asn Leu Asn Ile Thr Lys Thr Phe Thr Leu Ile Thr Asp Thr Asn
    50                 55                 60

Val Leu Val Ala Val Gly Glu Asn Glu Lys Thr Ile Tyr Val Val Phe
65                 70                 75                 80

Arg Gly Thr Ser Ser Ile Arg Asn Ala Ile Ala Asp Ile Val Phe Val
                85                 90                 95

Pro Val Asn Tyr Pro Pro Val Asn Gly Ala Lys Val His Lys Gly Phe
                100                105                110
```

```
Leu Asp Ser Tyr Asn Glu Val Gln Asp Lys Leu Val Ala Glu Val Lys
        115                 120                 125

Ala Gln Leu Asp Arg His Pro Gly Tyr Lys Ile Val Val Thr Gly His
    130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                165                 170                 175

Gly Thr Pro Glu Phe Ala Asn Tyr Val Ile Gly Thr Lys Ile Pro Tyr
            180                 185                 190

Gln Arg Leu Val Asn Glu Arg Asp Ile Val Pro His Leu Pro Pro Gly
        195                 200                 205

Ala Phe Gly Phe Leu His Ala Gly Glu Glu Phe Trp Ile Met Lys Asp
    210                 215                 220

Ser Ser Leu Arg Val Cys Pro Asn Gly Ile Glu Thr Asp Asn Cys Ser
225                 230                 235                 240

Asn Ser Ile Val Pro Phe Thr Ser Val Ile Asp His Leu Ser Tyr Leu
                245                 250                 255

Asp Met Asn Thr Gly Leu Cys Leu
            260

<210> SEQ ID NO 5
<211> LENGTH: 269
<212> TYPE: PRT
<213> ORGANISM: Rhizomucor miehei

<400> SEQUENCE: 5

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45

Leu Lys Ile Ile Lys Thr Trp Ser Thr Leu Ile Tyr Asp Thr Asn Ala
    50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
    130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
    210                 215                 220
```

```
Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
            245                 250                 255

His Leu Ser Tyr Phe Gly Ile Asn Thr Gly Leu Cys Thr
        260                 265
```

<210> SEQ ID NO 6
<211> LENGTH: 271
<212> TYPE: PRT
<213> ORGANISM: Rhizopus oryzae

<400> SEQUENCE: 6

```
Ser Ala Ser Asp Gly Gly Lys Val Val Ala Thr Thr Ala Gln Ile
1               5                   10                  15

Gln Glu Phe Thr Lys Tyr Ala Gly Ile Ala Ala Thr Ala Tyr Cys Arg
            20                  25                  30

Ser Val Val Pro Gly Asn Lys Trp Asp Cys Val Gln Cys Gln Lys Trp
        35                  40                  45

Val Pro Asp Gly Lys Ile Ile Thr Thr Phe Thr Ser Leu Leu Ser Asp
    50                  55                  60

Thr Asn Gly Tyr Val Leu Arg Ser Asp Lys Gln Lys Thr Ile Tyr Leu
65                  70                  75                  80

Val Phe Arg Gly Thr Asn Ser Phe Arg Ser Ala Ile Thr Asp Ile Val
                85                  90                  95

Phe Asn Phe Ser Asp Tyr Lys Pro Val Lys Gly Ala Lys Val His Ala
            100                 105                 110

Gly Phe Leu Ser Ser Tyr Glu Gln Val Val Asn Asp Tyr Phe Pro Val
        115                 120                 125

Val Gln Glu Gln Leu Thr Ala His Pro Thr Tyr Lys Val Ile Val Thr
    130                 135                 140

Gly His Ser Leu Gly Gly Ala Gln Ala Leu Leu Ala Gly Met Asp Leu
145                 150                 155                 160

Tyr Gln Arg Glu Pro Arg Leu Ser Pro Lys Asn Leu Ser Ile Phe Thr
                165                 170                 175

Val Gly Gly Pro Arg Val Gly Asn Pro Thr Phe Ala Tyr Tyr Val Glu
            180                 185                 190

Ser Thr Gly Ile Pro Phe Gln Arg Thr Val His Lys Arg Asp Ile Val
        195                 200                 205

Pro His Val Pro Pro Gln Ser Phe Gly Phe Leu His Pro Gly Val Glu
    210                 215                 220

Ser Trp Ile Lys Ser Gly Thr Ser Asn Val Gln Ile Cys Thr Ser Glu
225                 230                 235                 240

Ile Glu Thr Lys Asp Cys Ser Asn Ser Ile Val Pro Phe Thr Ser Ile
                245                 250                 255

Leu Asp His Leu Ser Tyr Phe Asp Ile Asn Glu Gly Ser Cys Leu
            260                 265                 270
```

<210> SEQ ID NO 7
<211> LENGTH: 267
<212> TYPE: PRT
<213> ORGANISM: Aspergillus niger

<400> SEQUENCE: 7

```
Thr Ala Gly His Ala Leu Ala Ala Ser Thr Gln Gly Ile Ser Glu Asp
1               5                   10                  15
```

```
Leu Tyr Ser Arg Leu Val Glu Met Ala Thr Ile Ser Gln Ala Ala Tyr
             20                  25                  30

Ala Asp Leu Cys Asn Ile Pro Ser Thr Ile Ile Lys Gly Glu Lys Ile
             35                  40                  45

Tyr Asn Ser Gln Thr Asp Ile Asn Gly Trp Ile Leu Arg Asp Asp Ser
         50                  55                  60

Ser Lys Glu Ile Ile Thr Val Phe Arg Gly Thr Gly Ser Asp Thr Asn
 65                  70                  75                  80

Leu Gln Leu Asp Thr Asn Tyr Thr Leu Thr Pro Phe Asp Thr Leu Pro
                 85                  90                  95

Gln Cys Asn Gly Cys Glu Val His Gly Gly Tyr Tyr Ile Gly Trp Val
            100                 105                 110

Ser Val Gln Asp Gln Val Glu Ser Leu Val Lys Gln Gln Val Ser Gln
            115                 120                 125

Tyr Pro Asp Tyr Ala Leu Thr Val Thr Gly His Ser Leu Gly Ala Ser
            130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Gly Asn Gln Ala Phe Ala
                165                 170                 175

Ser Tyr Met Asn Asp Ala Phe Gln Ala Ser Ser Pro Asp Thr Thr Gln
            180                 185                 190

Tyr Phe Arg Val Thr His Ala Asn Asp Gly Ile Pro Asn Leu Pro Pro
        195                 200                 205

Val Glu Gln Gly Tyr Ala His Gly Gly Val Glu Tyr Trp Ser Val Asp
    210                 215                 220

Pro Tyr Ser Ala Gln Asn Thr Phe Val Cys Thr Gly Asp Glu Val Gln
225                 230                 235                 240

Cys Cys Glu Ala Gln Gly Gly Gln Gly Val Asn Asn Ala His Thr Thr
                245                 250                 255

Tyr Phe Gly Met Thr Ser Gly Ala Cys Thr Trp
            260                 265

<210> SEQ ID NO 8
<211> LENGTH: 266
<212> TYPE: PRT
<213> ORGANISM: Aspergillus tubingensis

<400> SEQUENCE: 8

Thr Ala Gly His Ala Leu Ala Ala Ser Thr Gln Gly Ile Ser Glu Asp
  1               5                  10                  15

Leu Tyr Ser Arg Leu Val Glu Met Ala Thr Ile Ser Gln Ala Ala Tyr
             20                  25                  30

Ala Asp Leu Cys Asn Ile Pro Ser Thr Ile Ile Lys Gly Glu Lys Ile
             35                  40                  45

Tyr Asn Ser Gln Thr Asp Ile Asn Gly Trp Ile Leu Arg Asp Asp Ser
         50                  55                  60

Ser Lys Glu Ile Ile Thr Val Phe Arg Gly Thr Gly Ser Asp Thr Asn
 65                  70                  75                  80

Leu Gln Leu Asp Thr Asn Tyr Thr Leu Thr Pro Phe Asp Thr Leu Pro
                 85                  90                  95

Gln Cys Asn Ser Cys Glu Val His Gly Gly Tyr Tyr Ile Gly Trp Ile
            100                 105                 110

Ser Val Gln Asp Gln Val Glu Ser Leu Val Gln Gln Gln Val Ser Gln
```

-continued

```
                115                 120                 125
Phe Pro Asp Tyr Ala Leu Thr Val Thr Gly His Ser Leu Gly Ala Ser
    130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Asn Gln Ala Phe Ala Ser
                165                 170                 175

Tyr Met Asn Asp Ala Phe Gln Ala Ser Ser Pro Asp Thr Thr Gln Tyr
            180                 185                 190

Phe Arg Val Thr His Ala Asn Asp Gly Ile Pro Asn Leu Pro Pro Ala
        195                 200                 205

Asp Glu Gly Tyr Ala His Gly Val Val Glu Tyr Trp Ser Val Asp Pro
    210                 215                 220

Tyr Ser Ala Gln Asn Thr Phe Val Cys Thr Gly Asp Glu Val Gln Cys
225                 230                 235                 240

Cys Glu Ala Gln Gly Gly Gln Gly Val Asn Asn Ala His Thr Thr Tyr
                245                 250                 255

Phe Gly Met Thr Ser Gly His Cys Thr Trp
            260                 265
```

<210> SEQ ID NO 9
<211> LENGTH: 275
<212> TYPE: PRT
<213> ORGANISM: Fusarium heterosporum

<400> SEQUENCE: 9

```
Ala Val Thr Val Thr Thr Gln Asp Leu Ser Asn Phe Arg Phe Tyr Leu
1               5                   10                  15

Gln His Ala Asp Ala Ala Tyr Cys Asn Phe Asn Thr Ala Val Gly Lys
                20                  25                  30

Pro Val His Cys Ser Ala Gly Asn Cys Pro Asp Ile Glu Lys Asp Ala
            35                  40                  45

Ala Ile Val Val Gly Ser Val Gly Thr Lys Thr Gly Ile Gly Ala
    50                  55                  60

Tyr Val Ala Thr Asp Asn Ala Arg Lys Glu Ile Val Val Ser Val Arg
65                  70                  75                  80

Gly Ser Ile Asn Val Arg Asn Trp Ile Thr Asn Phe Asn Phe Gly Gln
                85                  90                  95

Lys Thr Cys Asp Leu Val Ala Gly Cys Gly Val His Thr Gly Phe Leu
            100                 105                 110

Asp Ala Trp Glu Glu Val Ala Ala Asn Val Lys Ala Ala Val Ser Ala
        115                 120                 125

Ala Lys Thr Ala Asn Pro Thr Phe Lys Phe Val Val Thr Gly His Ser
    130                 135                 140

Leu Gly Gly Ala Val Ala Thr Ile Ala Ala Ala Tyr Leu Arg Lys Asp
145                 150                 155                 160

Gly Phe Pro Phe Asp Leu Tyr Thr Tyr Gly Ser Pro Arg Val Gly Asn
                165                 170                 175

Asp Phe Phe Ala Asn Phe Val Thr Gln Gln Thr Gly Ala Glu Tyr Arg
            180                 185                 190

Val Thr His Gly Asp Asp Pro Val Pro Arg Leu Pro Pro Ile Val Phe
        195                 200                 205

Gly Tyr Arg His Thr Ser Pro Glu Tyr Trp Leu Asn Gly Gly Pro Leu
    210                 215                 220
```

```
Asp Lys Asp Tyr Thr Val Thr Glu Ile Lys Val Cys Glu Gly Ile Ala
225                 230                 235                 240

Asn Val Met Cys Asn Gly Gly Thr Ile Gly Leu Asp Ile Leu Ala His
            245                 250                 255

Ile Thr Tyr Phe Gln Ser Met Ala Thr Cys Ala Pro Ile Ala Ile Pro
            260                 265                 270

Trp Lys Arg
        275

<210> SEQ ID NO 10
<211> LENGTH: 278
<212> TYPE: PRT
<213> ORGANISM: Aspergillus oryzae

<400> SEQUENCE: 10

Asp Ile Pro Thr Thr Gln Leu Glu Asp Phe Lys Phe Trp Val Gln Tyr
1               5                   10                  15

Ala Ala Ala Thr Tyr Cys Pro Asn Asn Tyr Val Ala Lys Asp Gly Glu
            20                  25                  30

Lys Leu Asn Cys Ser Val Gly Asn Cys Pro Asp Val Glu Ala Ala Gly
            35                  40                  45

Ser Thr Val Lys Leu Ser Phe Ser Asp Thr Ile Thr Asp Thr Ala
50                  55                  60

Gly Phe Val Ala Val Asp Asn Thr Asn Lys Ala Ile Val Val Ala Phe
65                  70                  75                  80

Arg Gly Ser Tyr Ser Ile Arg Asn Trp Val Thr Asp Ala Thr Phe Pro
                85                  90                  95

Gln Thr Asp Pro Gly Leu Cys Asp Gly Cys Lys Ala Glu Leu Gly Phe
            100                 105                 110

Trp Thr Ala Trp Lys Val Val Arg Asp Arg Ile Ile Lys Thr Leu Asp
            115                 120                 125

Glu Leu Lys Pro Glu His Ser Asp Tyr Lys Ile Val Val Gly His
130                 135                 140

Ser Leu Gly Ala Ala Ile Ala Ser Leu Ala Ala Ala Asp Leu Arg Thr
145                 150                 155                 160

Lys Asn Tyr Asp Ala Ile Leu Tyr Ala Tyr Ala Ala Pro Arg Val Ala
                165                 170                 175

Asn Lys Pro Leu Ala Glu Phe Ile Thr Asn Gln Gly Asn Asn Tyr Arg
            180                 185                 190

Phe Thr His Asn Asp Asp Pro Val Pro Lys Leu Pro Leu Leu Thr Met
            195                 200                 205

Gly Tyr Val His Ile Ser Pro Glu Tyr Tyr Ile Thr Ala Pro Asp Asn
210                 215                 220

Thr Thr Val Thr Asp Asn Gln Val Thr Val Leu Asp Gly Tyr Val Asn
225                 230                 235                 240

Phe Lys Gly Asn Thr Gly Thr Ser Gly Gly Leu Pro Asp Leu Leu Ala
                245                 250                 255

Phe His Ser His Val Trp Tyr Phe Ile His Ala Asp Ala Cys Lys Gly
            260                 265                 270

Pro Gly Leu Pro Leu Arg
        275

<210> SEQ ID NO 11
<211> LENGTH: 278
<212> TYPE: PRT
<213> ORGANISM: Penicillium camemberti
```

<400> SEQUENCE: 11

Asp Val Ser Thr Ser Glu Leu Asp Gln Phe Glu Phe Trp Val Gln Tyr
1               5                   10                  15

Ala Ala Ala Ser Tyr Glu Ala Asp Tyr Thr Ala Gln Val Gly Asp
            20                  25                  30

Lys Leu Ser Cys Ser Lys Gly Asn Cys Pro Glu Val Glu Ala Thr Gly
            35                  40                  45

Ala Thr Val Ser Tyr Asp Phe Ser Asp Ser Thr Ile Thr Asp Thr Ala
        50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
            115                 120                 125

Glu Val Val Ala Gln Asn Pro Asn Tyr Glu Leu Val Val Val Gly His
        130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175

Gly Asn Ala Ala Leu Ala Lys Tyr Ile Thr Ala Gln Gly Asn Asn Phe
            180                 185                 190

Arg Phe Thr His Thr Asn Asp Pro Val Pro Lys Leu Pro Leu Leu Ser
            195                 200                 205

Met Gly Tyr Val His Val Ser Pro Glu Tyr Trp Ile Thr Ser Pro Asn
        210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
            260                 265                 270

Gly Leu Pro Phe Lys Arg
        275

<210> SEQ ID NO 12
<211> LENGTH: 270
<212> TYPE: PRT
<213> ORGANISM: Aspergillus foetidus

<400> SEQUENCE: 12

Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser Lys Asp Ser Asn
            20                  25                  30

Leu Thr Cys Thr Ala Asn Ala Cys Pro Ser Val Glu Glu Ala Ser Thr
            35                  40                  45

Thr Met Leu Leu Glu Phe Asp Leu Thr Asn Asp Phe Gly Gly Thr Ala
        50                  55                  60

Gly Phe Leu Ala Ala Asp Asn Thr Asn Lys Arg Leu Val Val Ala Phe
65                  70                  75                  80

```
Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
            100                 105                 110

Phe Trp Lys Ala Trp Glu Ser Ala Ala Asp Glu Leu Thr Ser Lys Ile
        115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
    210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                245                 250                 255

Ala His Leu Trp Tyr Phe Phe Ala Ile Ser Glu Cys Leu Leu
            260                 265                 270

<210> SEQ ID NO 13
<211> LENGTH: 270
<212> TYPE: PRT
<213> ORGANISM: Aspergillus niger

<400> SEQUENCE: 13

Ser Val Ser Thr Ser Thr Leu Asp Glu Leu Gln Leu Phe Ser Gln Trp
1               5                   10                  15

Ser Ala Ala Ala Tyr Cys Ser Asn Asn Ile Asp Ser Asp Asp Ser Asn
                20                  25                  30

Val Thr Cys Thr Ala Asp Ala Cys Pro Ser Val Glu Glu Ala Ser Thr
            35                  40                  45

Lys Met Leu Leu Glu Phe Asp Leu Thr Asn Asn Phe Gly Gly Thr Ala
    50                  55                  60

Gly Phe Leu Ala Ala Asp Asn Thr Asn Lys Arg Leu Val Val Ala Phe
65                  70                  75                  80

Arg Gly Ser Ser Thr Ile Lys Asn Trp Ile Ala Asp Leu Asp Phe Ile
                85                  90                  95

Leu Gln Asp Asn Asp Asp Leu Cys Thr Gly Cys Lys Val His Thr Gly
            100                 105                 110

Phe Trp Lys Ala Trp Glu Ala Ala Ala Asp Asn Leu Thr Ser Lys Ile
        115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Val
                165                 170                 175

Gly Asn Tyr Ala Leu Ala Glu His Ile Thr Ser Gln Gly Ser Gly Ala
```

```
                180             185             190
Asn Phe Pro Val Thr His Leu Asn Asp Ile Val Pro Arg Val Pro Pro
            195                 200                 205

Met Asp Phe Gly Phe Ser Gln Pro Ser Pro Glu Tyr Trp Ile Thr Ser
            210                 215                 220

Gly Thr Gly Ala Ser Val Thr Ala Ser Asp Ile Glu Leu Ile Glu Gly
225                 230                 235                 240

Ile Asn Ser Thr Ala Gly Asn Ala Gly Glu Ala Thr Val Asp Val Leu
                245                 250                 255

Ala His Leu Trp Tyr Phe Phe Ala Ile Ser Glu Cys Leu Leu
            260                 265                 270

<210> SEQ ID NO 14
<211> LENGTH: 269
<212> TYPE: PRT
<213> ORGANISM: Aspergillus oryzae

<400> SEQUENCE: 14

Asp Val Ser Ser Leu Leu Asn Asn Leu Asp Leu Phe Ala Gln Tyr
1               5                   10                  15

Ser Ala Ala Ala Tyr Cys Asp Glu Asn Leu Asn Ser Thr Gly Thr Lys
            20                  25                  30

Leu Thr Cys Ser Val Gly Asn Cys Pro Leu Val Glu Ala Ala Ser Thr
        35                  40                  45

Gln Ser Leu Asp Glu Phe Asn Glu Ser Ser Tyr Gly Asn Pro Ala
    50                  55                  60

Gly Tyr Leu Ala Ala Asp Glu Thr Asn Lys Leu Leu Val Leu Ser Phe
65                  70                  75                  80

Arg Gly Ser Ala Asp Leu Ala Asn Trp Val Ala Asn Leu Asn Phe Gly
                85                  90                  95

Leu Glu Asp Ala Ser Asp Leu Cys Ser Gly Cys Glu Val His Ser Gly
            100                 105                 110

Phe Trp Lys Ala Trp Ser Glu Ile Ala Asp Thr Ile Thr Ser Lys Val
        115                 120                 125

Glu Ser Ala Leu Ser Asp His Ser Asp Tyr Ser Leu Val Leu Thr Gly
    130                 135                 140

His Ser Tyr Gly Ala Ala Leu Ala Ala Leu Ala Ala Thr Ala Leu Arg
145                 150                 155                 160

Asn Ser Gly His Ser Val Glu Leu Tyr Asn Tyr Gly Gln Pro Arg Leu
                165                 170                 175

Gly Asn Glu Ala Leu Ala Thr Tyr Ile Thr Asp Gln Asn Lys Gly Gly
            180                 185                 190

Asn Tyr Arg Val Thr His Thr Asn Asp Ile Val Pro Lys Leu Pro Pro
        195                 200                 205

Thr Leu Leu Gly Tyr His His Phe Ser Pro Glu Tyr Tyr Ile Ser Ser
    210                 215                 220

Ala Asp Glu Ala Thr Val Thr Thr Asp Val Thr Glu Val Thr Gly
225                 230                 235                 240

Ile Asp Ala Thr Gly Gly Asn Asp Gly Thr Asp Gly Thr Ser Ile Asp
                245                 250                 255

Ala His Arg Trp Tyr Phe Ile Tyr Ile Ser Glu Cys Ser
            260                 265

<210> SEQ ID NO 15
<211> LENGTH: 269
```

```
-continued

<212> TYPE: PRT
<213> ORGANISM: Thermomyces lanuginosus

<400> SEQUENCE: 15

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
                100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
    195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260                 265
```

US 7,465,570 B2

VARIANT LIPOLYTIC ENZYMES

CROSS-REFERENCE TO RELATED APPLICATIONS

This application is a 35 U.S.C. 371 national application of PCT/DK2004/000292 filed Apr. 29, 2004, which claims priority or the benefit under 35 U.S.C. 119 of Danish application nos. PA 2003 00709 filed May 9, 2003 and PA 2003 00811 filed May 30, 2003 and U.S. Provisional application Nos. 60/469,228, 60/474,881 and 60/479,647 filed May 9, 2003, May 30, 2003, and Jun. 19, 2003, respectively, the contents of which are fully incorporated herein by reference.

FIELD OF INVENTION

The present invention relates to variant polypeptides made by altering the amino acid sequence of a fungal lipolytic enzyme, particularly to such polypeptides with improved properties for use in a dough, e.g. for making bread and other baked products, and more particularly to such polypeptides having hydrolytic activity towards ester bonds in polar lipids.

BACKGROUND OF THE INVENTION

Phospholipases and galactolipases are known as enzymes with hydrolytic activity towards ester bonds in polar lipids such as phospholipids and galactolipids. WO 0032758 discloses lipolytic enzyme variants having phospholipase and galactolipase activity and their use in baking. WO 9826057 discloses a lipase/phospholipase from *Fusarium oxysporum* and its use in baking. WO 0183770 describes variants of a fungal lipase.

SUMMARY OF THE INVENTION

The inventors have developed variant polypeptides by modifying the amino acid sequence of a parent polypeptide which is a fungal lipolytic enzymes. The variant polypeptides result in a reduced dough stickiness, compared to the parent polypeptide, when they are added to a dough.

Accordingly, the invention provides a method of producing a polypeptide, comprising:

a) selecting an amino acid sequence for a parent polypeptide which is a fungal lipolytic enzyme, b) selecting an amino acid residue in the sequence which corresponds to A29, K33, I83 or A255 of SEQ ID NO: 1 (corresponding to P29, N33, R84 or P256 of SEQ ID NO: 2), c) modifying the amino acid sequence by substituting or deleting the selected residue, d) preparing a variant polypeptide having the modified amino acid sequence, and e) adding the polypeptide to a dough and testing dough stickiness.

The invention also provides a variant polypeptide which:

a) has hydrolytic activity towards an ester bonds in a polar lipid, and b) has an amino acid sequence which i) has at least 80% identity to SEQ ID NO: 1 and has a different amino acid or an amino acid deletion at a position corresponding to A29, K33, I83 or A255, or ii) has at least 80% identity to SEQ ID NO: 2 and has a different amino acid or an amino acid deletion at a position corresponding to R84 or P256.

BRIEF DESCRIPTION OF DRAWINGS

FIG. 1 shows an alignment of amino acid sequences of fungal lipolytic enzymes to identify corresponding amino acids in SEQ ID NO: 1 to 15. SEQ ID NO: 1 is the lipase/phospholipase from *Fusarium oxysporum* (WO 9826057). SEQ ID NO: 2 is a variant with phospholipase and galactolipase activity disclosed in WO 0032758. SEQ ID NO: 3 to 15 are known lipolytic enzymes from the following organisms: *Absidia reflexa, Absidia corymbefera, Rhizomucor miehei, Rhizopus delemar (oryzae), Aspergillus niger, Aspergillus tubingensis, Fusarium heterosporum, Aspergillus oryzae, Penicilium camemberti, Aspergillus foetidus, Aspergillus niger, Aspergillus oryzae* and *Thermomyces lanuginosus*.

DETAILED DESCRIPTION OF THE INVENTION

Parent Polypeptide

The parent polypeptide may have the sequence SEQ ID NO: 1 or 2 or one which can be aligned with SEQ ID NO: 1 or 2. It may have at least 50% amino acid identity to SEQ ID NO: 1 or 2, e.g. at least 60%, at least 70% or at least 80%. Examples are the polypeptides having the sequences SEQ ID NO: 1 to 14 or a variant disclosed in WO 0032758.

The parent polypeptide has lipolytic enzyme activity, e.g. hydrolytic activity towards an ester bond in a polar lipid.

Variant Polypeptide

The amino acid at the position corresponding to A29 in SEQ ID NO: 1 may be P. The amino acid at the position corresponding to K33 in SEQ ID NO: 1 may be N. The amino acid at the position corresponding to I83 of SEQ ID NO: 1 may be A/R/N/D/C/Q/E/G/H/L/K/M/F/P/S/T/Y/V. The amino acid at the position corresponding to A255 in SEQ ID NO: 1 may be R/N/D/C/Q/E/G/H/I/L/K/M/F/P/S/T/W/Y/V.

The amino acid at the position corresponding to R84 of SEQ ID NO: 2 may be A/N/D/C/Q/E/G/H/I/L/K/M/F/P/S/T/Y/V. The amino acid at the position corresponding to P256 in SEQ ID NO: 2 may be A/R/N/D/C/Q/E/G/H/I/L/K/M/F/S/T/W/Y/V. The polypeptide may comprise further modifications compared to SEQ ID NO: 2., e.g. as disclosed in WO 0032758. Thus, it may have the amino acid A/T at position D62, G/T at position A91, D/F/S/G at position W96, E at position K99, G at position S158, D at position G240, S at position N247, D at position N248, K/R at position Q249, K/T at position P250, T at position N251, F at position I252, M/R at position P253, S/Y/W at position D254, L at position I255, G at position A257, H/C at position W260, G at position Q263, L at position A264, I at position T265, G/S/A at position D266, T at position A267, L at position N269 and/or truncation after N269.

The polypeptide may additionally comprise amino acid modifications such as insertions or deletions. Also, the N- or C-terminus may be modified, e.g. by truncating residues in SEQ ID NO: 2 after position 269 or by extending the C-terminal of SEQ ID NO: 2 with WRRYRSAESVDKRATMT-DAELEKKLNSYVQMDKEYVKNNQARS. The C-terminal may be truncated after position 272, 273, 274 or 286 in SEQ ID NO: 1. The N-terminal may have a peptide extension, e.g. as described in WO 0032758 or WO 9704079, such as the addition of the amino acid residues SPIRR.

A similar amino acid substitution or deletion may be made in other fungal lipolytic enzymes, e.g. SEQ ID NO: 3-14 at a corresponding position. The corresponding positions may be found by aligning a given sequence with SEQ ID NO: 1 or 2, e.g. as shown in FIG. 1. The alignment may be done by use of the GAP program as described below.

The variant polypeptide may have improved thermostability compared to the parent polypeptide, particularly a variant polypeptide having a substitution at a position corresponding to A29 or K33 of SEQ ID NO: 1, e.g. the substitution A29P or K33N.

Sequence Identity

The variant polypeptide has at least 80% identity to SEQ ID NO: 1 or 2, particularly at least 85%, at least 90%, at least 95%, or at least 98%. The degree of identity between two sequences may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

Dough Stickiness

The variant polypeptide may be tested by adding it to a dough and evaluating the dough stickiness. The dough may be generated according to a typical European straight dough procedure, a typical American sponge & dough procedure or any other bread making procedures. The polypeptide may be added at a dosage of 0.01-10 mg enzyme protein per kg flour, and the dough stickiness may be evaluated directly after mixing or at any point during processing. Of particular importance is the dough stickiness of the finally mixed dough, i.e. at the time where the dough runs through processing equipment such as divider, molder, sheeter and conveyor belts. The mixing time varies depending on procedure. For a typical European straight dough procedure, the mixing time can e.g. be in the range of 6-10 minutes. For a typical American Sponge & dough procedure the mixing time can e.g. be in the range of 6-20 minutes (on final dough). The dough may have a resting period of 5-20 min before further processing, e.g. at 20-35° C. The dough stickiness may be evaluated by hand by trained bakers, by a sensory panel or by instrumental measurements e.g. by the Chen-Hoseney dough stickiness rig developed for Stable Micro Systems TA-XT2 texture analyser, commercially available from Brookfield Engineering Laboratories, Inc.

Hydrolytic Activity towards Ester Bonds in Polar Lipids

The parent and variant polypeptides have lipolytic enzyme activity, i.e. they have hydrolytic activity towards an ester bond and are classified in EC 3.1.1 Carboxylic Ester Hydrolases according to Enzyme Nomenclature (available at www.chem.qmw.ac.uk/iubmb/enzyme). More specifically, they have hydrolytic activity towards ester bonds in polar lipids so as to split off acyl groups at the sn-1 and/or sn-2 position of polar lipids such as phospholipids and galactolipids. Accordingly, they may have phospholipase activity or galactolipase activity (EC 3.1.1.26), e.g. phospholipase A1 activity (EC 3.1.1.32).

Phospholipase activity may be determined by known methods, e.g. the "monolayer phospholipase assay" or the plate assay described in WO 0032758. Galactolipase activity may be determined with digalactosyl diglyceride as substrate, e.g. as described in WO 0032758.

Use of Polypeptide

The polypeptide may be added to a dough, and the dough may be used to prepare a steamed bread, a baked product (particularly bread), pasta or noodles. The addition of the polypeptide may lead to improved dough stabilization, i.e. a larger loaf volume of the baked product and/or a better shape retention and volume during processing and baking, particularly in a stressed system, e.g. in the case of over-proofing or over-mixing. It may also lead to a lower initial firmness and/or a more uniform and fine crumb, improved crumb structure (finer crumb, thinner cell walls, more rounded cells), of the baked product, and it may further improve dough properties, e.g. a less soft dough, higher elasticity and/or lower extensibility.

The process may be conducted in analogy with U.S. Pat. No. 5,578,489 or U.S. Pat. No. 6,077,336. In the case of un-proofed frozen dough the polypeptides of the invention perform better than known lipolytic enzyme variants in terms of volume and crumb structure.

The polypeptide can be used in a process for making bread, comprising adding the polypeptide to the ingredients of a dough, kneading the dough and baking the dough to make the bread. This can be done in analogy with U.S. Pat. No. 4,567,046 (Kyowa Hakko), JP-A 60-78529 (QP Corp.), JP-A 62-111629 (QP Corp.), JP-A 63-258528 (QP Corp.), EP 426211 (Unilever) or WO 99/53769 (Novozymes).

The composition of a typical dough can be found in WO 99/53769.

The polypeptide of the invention may be added together with an anti-staling amylase and optionally also a phospholipid as described in WO 9953769, particularly a maltogenic alpha-amylase (e.g. from *Bacillus* sp., such as Novamyl® from Novo Nordisk). Also, a fungal or bacterial α-amylase may be added, e.g. from *Aspergillus* or *Bacillus*, particularly *A. oryzae, B. licheniformis* or *B. amyloliquefaciens*. Optionally an additional enzyme may be added, e.g. an amyloglucosidase, a beta-amylase, a pentosanase such as a xylanase as described in WO 99/53769, e.g. derived from *Aspergillus*, in particular of *A. aculeatus, A. niger* (cf. WO 91/19782), *A. awamori* (WO 91/18977), or *A. tubigensis* (WO 92/01793), from a strain of *Trichoderma*, e.g. *T. reesei*, or from a strain of *Humicula*, e.g. *H. insolens* (WO 92/17573), a proteiase and/or a glucose oxidase.

The dough may further comprise an emulsifier such as mono- or diglycerides, diacyl tartaric acid esters of mono- or diglycerides, sugar esters of fatty acids, polyglycerol esters of fatty acids, lactic esters of monoglycerides, acetic acid esters of monoglycerides, polyoxyethylene stearates, polysorbates or lysolecithin.

The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

EXAMPLES

Baking Evaluation of Polypeptides with Phospholipase Activity

In the examples, polypeptides according to the invention were tested together with the corresponding parent polypeptide in a baking evaluation experiment by using conventional baking protocols for European straight dough procedure and US sponge & dough procedure, as follows:

European Straight Dough Procedure:

A dough is prepared by mixing the below ingredients for 3 minutes slow and 7 minutes fast.

|  | % (baker's - by weight) |
| --- | --- |
| Flour | 100 |
| Compressed yeast | 4 |
| Salt | 1.5 |
| Sugar | 1.5 |
| Water | 62 |
| Ascorbic acid | 40 ppm |

Dough stickiness is evaluated right after mixing and again after a resting period of 15 minutes. Dough stickiness is evaluated by a trained and experienced bakers by sensory evaluation by hand. Dough stickiness is a measure of how sticky the dough feels and is expressed on a scale from 0 (little stickiness) to 10 (very sticky). The dough with the variant is compared to a reference dough, which is always given the score 5.

Sponge & Dough Procedure:

|  | Sponge % (baker's - by weight) | Dough % (baker's - by weight) |
| --- | --- | --- |
| Flour | 60 | 40 |
| Compressed yeast | 7.5 | |
| Oil | 2.5 | |
| Salt | | 2 |
| High fructose syrup | | 12 |
| Water | 34.4 | 20.4 |
| Ascorbicc acid | | 50 |

A liquid sponge is prepared by mixing a sponge consisting of the above listed sponge ingredients for 1 minute slow and 4 minutes fast. The sponge is fermented for 3 hours at 27 C, 86% RH. The sponge is mixed with the dough ingredients listed above and with enzymes for 1 minutes slow and 18 minutes fast.

Dough stickiness is evaluated right after mixing, whereafter the dough is extruded on a rebuild pasta-machine to simulate the dough extrusion used for dough dividing in US. Dough stickiness is evaluated again after extrusion. Dough stickiness is evaluated by a trained and experienced bakers by sensory evaluation by hand. Dough stickiness is a measure of how sticky the dough feels and is expressed on a scale from 0 (little stickiness) to 10 (very sticky). The dough with the variant polypeptide is compared to a reference dough made with the parent polypeptide, which is always given the score 5.

Example 1

Construction of Polypeptides

Polypeptides according to the invention were prepared as described in WO 00/32758. The polypeptides were derived from SEQ ID NO: 15 by making the following amino acid modifications.

| Polypeptide | Amino acid alterations compared to SEQ ID NO: 15 |
| --- | --- |
| 1 | G91A +D96W +E99K +P256M +G263Q +L264A +I265T +G266D +T267A + L269N +270A +271G +272G +273F +274S + 275WRRYRSAESVDKRATMTDAELEKKLNSYVQMDKEYVKNNQARS |
| 2 | G91A +D96W +E99K +P256N +G263Q +L264A +I265T +G266D +T267A + L269N +270A +271G +272G +273F +274S + 275WRRYRSAESVDKRATMTDAELEKKLNSYVQMDKEYVKNNQARS |
| 3 | G91A +D96W +E99K +P256V +G263Q +L264A +I265T +G266D +T267A + L269N +270A +271G +272G +273F +274S + 275WRRYRSAESVDKRATMTDAELEKKLNSYVQMDKEYVKNNQARS |
| 4 | G91A +D96W +E99K +N247S +N248D +Q249K +N251T +P253M +D254S + P256L +A257A +G263Q +L264A +I265T +G266D +T267A +L269N |
| 5 | G91A +D96W +E99K +N247S +N248D +Q249R +P250T +N251T +P253M + D254W +P256V +A257G +G263Q +L264A +I265T +G266D +T267A + L269N |
| 6 | G91A +D96W +E99K +P256T +G263Q +L264A +I265T +G266D +T267A + L269N +270A +271G +272G +273F +274S + 275WRRYRSAESVDKRATMTDAELEKKLNSYVQMDKEYVKNNQARS |
| 7 | G91A +D96W +E99K +P256A +G263Q +L264A +I265T +G266D +T267A + L269N +270A +271G +272G +273F +274S + 275WRRYRSAESVDKRATMTDAELEKKLNSYVQMDKEYVKNNQARS |

-continued

| Polypeptide | Amino acid alterations compared to SEQ ID NO: 15 |
|---|---|
| 8 | G91A +D96W +E99K +G240D +P256C +G263Q +L264A +I265T +G266D + T267A +L269N +270A +271G +272G +273F +274S + 275WRRYRSAESVDKRATMTDAELEKKLNSYVQMDKEYVKNNQARS |
| 9 | G91A +D96W +E99K +P256G +G263Q +L264A +I265T +G266D +T267A + L269N +270A +271G +272G +273F +274S + 275WRRYRSAESVDKRATMTDAELEKKLNSYVQMDKEYVKNNQARS |
| 10 | G91A +D96W +E99K +P256R +G263Q +L264A +I265T +G266D +T267A + L269N +270A +271G +272G +273F +274S + 275WRRYRSAESVDKRATMTDAELEKKLNSYVQMDKEYVKNNQARS |
| 11 | G91A +D96W +E99K +P256Q +G263Q +L264A +I265T +G266D +T267A + L269N +270A +271G +272G +273F +274S + 275WRRYRSAESVDKRATMTDAELEKKLNSYVQMDKEYVKNNQARS |
| 12 | G91A +D96W +E99K +P256K +G263Q +L264A +I265T +G266D +T267A + L269N +270A +271G +272G +273F +274S + 275WRRYRSAESVDKRATMTDAELEKKLNSYVQMDKEYVKNNQARS |
| 13 | G91A +D96W +E99K +P256L +G263Q +L264A +I265T +G266D +T267A + L269N +270A +271G +272G +273F +274S + 275WRRYRSAESVDKRATMTDAELEKKLNSYVQMDKEYVKNNQARS |
| 14 | G91A +D96W +E99K +P256D +G263Q +L264A +I265T +G266D +T267A + L269N +270A +271G +272G +273F +274S + 275WRRYRSAESVDKRATMTDAELEKKLNSYVQMDKEYVKNNQARS |
| 15 | R84E +G91A +D96W +E99K +P256V +G263Q +L264A +I265T +G266D + T267A +L269N +270A +271G +272G +273F +274S + 275WRRYRSAESVDKRATMTDAELEKKLNSYVQMDKEYVKNNQARS |
| 16 | R84M +G91A +D96W +E99K +P256V +G263Q +L264A +I265T +G266D + T267A +L269N +270A +271G +272G +273F +274S + 275WRRYRSAESVDKRATMTDAELEKKLNSYVQMDKEYVKNNQARS |
| 17 | R84P +G91A +D96W +E99K +P256V +G263Q +L264A +I265T +G266D + T267A +L269N +270A +271G +272G +273F +274S + 275WRRYRSAESVDKRATMTDAELEKKLNSYVQMDKEYVKNNQARS |
| 18 | R84S +G91A +D96W +E99K +P256V +G263Q +L264A +I265T +G266D + T267A +L269N +270A +271G +272G +273F +274S + 275WRRYRSAESVDKRATMTDAELEKKLNSYVQMDKEYVKNNQARS |
| 19 | G91A +D96W +E99K +P250K +N251T +I252F +P253R +D254Y +I255L + P256del +G263Q +L264A +I265T +G266D +T267A +L269N +270A +271G + 272G +273F +274S + 275WRRYRSAESVDKRATMTDAELEKKLNSYVQMDKEYVKNNQARS |

Example 2

Baking Evaluation of a Polypeptide According to the Invention 5 variant polypeptides according to the invention were compared to the parent polypeptide (SEQ ID NO: 2) in the European straight dough procedure described above. 40 ppm Fungamyl Super MA (a blend of fungal alpha-amylase and xylanase) was added as background to all doughs. The parent enzyme and the variants were dosed at their optimal level, i.e. the level giving best volume and dough stabilising effect. The below results show that all 5 variants give reduced dough stickiness compared to the parent polypeptide.

| Polypeptide | Parent | P256V | P256A | P256Q | P256L | P256W |
|---|---|---|---|---|---|---|
| Dough stickiness after mixing | 6 | 5 | 5 | 5 | 5 | 5 |
| Dough stickiness after 15 min table time | 6 | 5 | 5 | 5 | 5 | 5 |

3 variant polypeptides according to the invention were compared to the parent polypeptide (SEQ ID NO: 1) in the European straight dough procedure described above. 40 ppm Fungamyl Super MA (a blend of fungal alpha-amylase and xylanase) was added as background to all doughs. The parent enzyme and the variants were dosed at their optimal level, i.e. the level giving best volume and dough stabilising effect. The below results show that all 4 variants give reduced dough stickiness compared to the parent enzyme

| Polypeptide | Parent | A29P+K33N+I83T | A29P+K33N+I83H | A29P+K33N+I83Q |
|---|---|---|---|---|
| Dough stickiness after mixing | 5 | 4 | 4 | 4 |
| Dough stickiness after 15 min table time | 5 | 4 | 4 | 4 |

4 variant polypeptides according to the invention were compared to the parent enzyme (SEQ ID NO: 1) in the European straight dough procedure described above. 10FAU Fungamyl/kg was added as background to all doughs. The parent enzyme and the variants were dosed at their optimal level, i.e. the level giving best volume and dough stabilising effect. The below results show that all 4 variants give reduced dough stickiness compared to the parent enzyme

| Polypeptide | Parent | A29P + K33N | A29P + I83N | K33N + I83E | K33N + I83K |
|---|---|---|---|---|---|
| Dough stickiness after mixing | 7 | 6 | 6 | 6 | 6 |
| Dough stickiness after 15 min table time | 7 | 6 | 6 | 6 | 6 |

A variant polypeptide according to the invention was compared to its parent enzyme (SEQ ID NO: 1) in the US sponge & dough procedure described above. 40 ppm Fungamyl Super MA (a blend of fungal alpha-amylase and xylanase) was added as background to all doughs. The parent enzyme and the variant were dosed at their optimal level, i.e. the level giving best volume and dough stabilising effect. The below results show that the variant gives reduced dough stickiness compared to the parent enzyme

| Polypeptide | Parent | A29P+I83N |
|---|---|---|
| Dough stickiness after mixing | 6 | 5 |
| Dough stickiness after extrusion | 6.5 | 5 |

Example 3

Variant Polypeptides Derived from SEQ ID NO: 1

Variant polypeptides with the following amino acid alterations compared SEQ ID NO: 1 (lipase/phospholipase from *F. oxysporum*) were prepared and tested by adding each polypeptide to a dough. The polypeptide with unmodified SEQ ID NO: 1 was also tested, for comparison.

A29P
K33N

-continued

A29P +I83T
A29P +I83N
A29P +I83C
A29P +I83F
A29P +I83L

-continued

K33N +I83W
K33N +I83L
K33N +I83Q
K33N +I83S
K33N +I83N
K33N +I83N
K33N +I83R
K33N +I83L
K33N +270VASLGDDTEAPRASTRGPP
A29P +I83N +A255V

The results were that with each of the above polypeptides, dough stickiness was better than with the polypeptide with the unmodified sequence of SEQ ID NO: 1.

Baking tests with each dough showed that all polypeptides improved the crumb structure, the loaf volume and the dough stability, both for the modified and unmodified sequences.

Example 4

Variant Polypeptides Derived from SEQ ID NO: 2

Variant polypeptides with the following amino acid alterations compared SEQ ID NO: 2 (variant of *T. lanuginosus* lipase) were prepared and tested by adding each polypeptide to a dough. The polypeptide with unmodified SEQ ID NO: 2 was also tested for comparison.

R84D
R84I
R84M
R84Q
P256A
P256D
P256I
P256L
P256Q
P256S
P256V

The results were that with each of the above polypeptides, dough stickiness was better than with the polypeptide with the unmodified sequence of SEQ ID NO: 2.

Baking tests with each dough showed that all polypeptides improved the crumb structure, the loaf volume and the dough stability, both for the modified and unmodified sequences.

The invention claimed is:

1. A variant polypeptide which has hydrolytic activity towards an ester bond in a polar lipid and comprises an amino acid sequence which has at least 95% identity to SEQ ID NO: 1 or 2 and comprises a substitution at position 29, 33, 83 or 255 with a different amino acid than originally present in the sequence, wherein (a) the substitution at position 29 is with a different amino acid; (b) the substitution at position 33 is with a different amino acid; (c) the substitution at position 83 is with Asp, Gln, or Met; (d) the substitution at position 255 is with Gln, Ile, Leu, or Val; and wherein each position corresponds to the position of the amino acid sequence of SEQ ID NO: 1.

2. The polypeptide of claim 1, wherein the polypeptide has phospholipase activity or galactolipase activity (EC 3.1.1.26).

3. The polypeptide of claim 1, which comprises an amino acid sequence which has at least 95% identity to SEQ ID NO: 1.

4. The polypeptide of claim 1, which comprises an amino acid sequence which has at least 95% identity to SEQ ID NO: 2.

5. The polypeptide of claim 3, which comprises a substitution at position 29.

6. The polypeptide of claim 5, wherein the substitution at position 29 is with Pro.

7. The polypeptide of claim 3, which comprises a substitution at position 33.

8. The polypeptide of claim 7, wherein the substitution at position 33 is with Asn.

9. The polypeptide of claim 3, which comprises a substitution at position 83 with Asp, Gln, or Met.

10. The polypeptide of claim 3, which comprises a substitution at position 255.

11. The polypeptide of claim 10, wherein the substitution at position 255 is with Val.

12. The polypeptide of claim 3, which comprises the sequence of amino acids 1-272, 1-273, 1-274 or 1-286 of SEQ ID NO: 1 and comprises:

```
A29P,
K33N
A29P +I83C,
A29P +I83F,
A29P +I83L,
K33N +I83N,
K33N +I83L +A255V,
K29P +I83T,
K33N +I83L,
K33N +I83N,
K33N +I83Q,
K33N +I83R,
K33N +I83S,
K33N +I83W, or
K33N +270VASLGDDTEAPRASTRGPP.
```

13. The polypeptide of claim 1, which further comprises
a substitution at position 62 with A or T;
a substitution at position 91 with G or T;
a substitution at position 99 with D, F, G, or S;
a substitution at position 99 with E;
a substitution at position 158 with G;
a substitution at position 240 with D;
a substitution at position 247 with S;
a substitution at position 248 with D;
a substitution at position 249 with K or R;
a substitution at position 250 with K or T;
a substitution at position 251 with T;
a substitution at position 252 with F;
a substitution at position 253 with M or R;
a substitution at position 254 with S, W, or Y;
a substitution at position 255 with L;
a substitution at position 257 with G;
a substitution at position 260 with H or C;
a substitution at position 263 with G;
a substitution at position 264 with L;
a substitution at position 265 with I;
a substitution at position 266 with A, G, or S;
a substitution at position 267 with T;
a substitution at position 269 with L; and/or
is truncated after position 269.

14. A method of producing a dough, comprising: adding a variant lipolytic enzyme of claim 1 to a dough.

15. The method of claim 14, Wherein said method further comprises baking the dough.

* * * * *